US008771369B2

(12) United States Patent
Yakimicki et al.

(10) Patent No.: US 8,771,369 B2
(45) Date of Patent: Jul. 8, 2014

(54) SURFACE MODIFICATION OF ULTRAHIGH MOLECULAR WEIGHT POLYETHYLENE

(75) Inventors: Donald L. Yakimicki, Warsaw, IN (US); Brian H. Thomas, Columbia City, IN (US); Lynn A. Kirkpatrick, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 278 days.

(21) Appl. No.: 12/749,743

(22) Filed: Mar. 30, 2010

(65) Prior Publication Data

US 2010/0249945 A1    Sep. 30, 2010

Related U.S. Application Data

(60) Provisional application No. 61/165,144, filed on Mar. 31, 2009.

(51) Int. Cl.
*A61F 2/28* (2006.01)
*A61L 33/00* (2006.01)

(52) U.S. Cl.
USPC ...................................... 623/23.58; 427/2.24

(58) Field of Classification Search
USPC ....................................................... 623/23.58
See application file for complete search history.

(56) References Cited

U.S. PATENT DOCUMENTS

| | | | |
|---|---|---|---|
| 3,353,988 A | | 11/1967 | Wolinski |
| 5,879,757 A | * | 3/1999 | Gutowski et al. ............. 427/491 |
| 6,051,751 A | * | 4/2000 | Sioshansi et al. ............. 128/898 |
| 6,448,315 B1 | | 9/2002 | Lidgren et al. |
| 7,214,764 B2 | | 5/2007 | King |
| 2003/0208278 A1 | | 11/2003 | Richard |
| 2005/0194722 A1 | | 9/2005 | Muratoglu et al. |
| 2005/0246021 A1 | | 11/2005 | Ringeisen et al. |
| 2006/0095039 A1 | | 5/2006 | Mutchler |
| 2006/0155383 A1 | | 7/2006 | Smith et al. |
| 2006/0258767 A1 | | 11/2006 | Schroeder et al. |
| 2007/0059334 A1 | | 3/2007 | Abt et al. |
| 2007/0067044 A1 | | 3/2007 | Hanes |
| 2008/0033573 A1 | | 2/2008 | King et al. |
| 2008/0036111 A1 | | 2/2008 | Sun |
| 2008/0125863 A1 | | 5/2008 | McKay |
| 2008/0319137 A1 | * | 12/2008 | Rufner et al. ............. 525/333.7 |

OTHER PUBLICATIONS

M.S. Silverstein, Surface Modification of UHMWPE Fibers, 1994, Journal of Applied Polymer Science, vol. 52, pp. 1785-1795.*

(Continued)

*Primary Examiner* — Bruce E Snow
*Assistant Examiner* — Brian Dukert
(74) *Attorney, Agent, or Firm* — Schwegman Lundberg & Woessner, P.A.

(57) ABSTRACT

The present invention relates to polymers and, specifically, to surface modification of polymers. In one exemplary embodiment, the present invention increases the bond strength of UHMWPE components to PMMA bone cement by creating a chemical bond between the UHMWPE components and the PMMA bone cement. Specifically, in one exemplary embodiment, a surface of the UHMWPE component that is to be bonded to PMMA bone cement is treated with an oxidizing agent, such as an aqueous solution of hydrogen peroxide. In one exemplary embodiment, the UHMWPE component is treated with hydrogen peroxide by swabbing the surface of the UHMWPE component with the hydrogen peroxide solution. The surface of the UHMWPE component may then be dried and PMMA bone cement applied to the surface of the UHMWPE component.

16 Claims, 2 Drawing Sheets

(56) References Cited

OTHER PUBLICATIONS

Dae Hyeok Yang et al.,"Surface and chemical properties of surface-modified UHMWPE powder and mechanical and thermal . . . ", Journal of Biomaterials Science, Polymer Edition, VSP, Utrecht, NL, vol. 16, No. 9, Jan. 1, 2005, pp. 1121-1138.

PCT International Search Report and Written Opinion of the International Searching Authority for PCT/US/2010/029137 dated Sep. 2, 2010.

Abstract of Article Surface modification of UHMPWE fibers, Silverstein et al., received Aug. 17, 1993 Wiley InterScience (Silverstein).

Abstract of Article Surface modification of UHMWPE fibers using enzyme as catalyst, Zhao et al., Fuhe Cailiao Xuebao, vol. 21, No. 4, pp. 62-66, Jul.-Aug. 2004, CSA Illumina (Zhao).

Article Visualization of room temperature polyethylene fibers surface restructuring induced by plasma selective etching, Intrater et al., date unknown (Intrater).

Article Surface Modification of Polyethylene, Desai et al., Advance Polymer Science 2004 vol. 169, pp. 231-293 (Desai).

PCT International Preliminary Report on Patentability for PCT/US2010/029137 dated Jun. 28, 2011.

"Chinese Application Serial No. 201080015080.8, Office Action mailed Jan. 25, 2013", English Translation, 4 pgs.

"Chinese Application Serial No. 201080015080.8, Response filed Apr. 21, 2013 to Office Action mailed Jan. 25, 2013", w/English claims, 11 pgs.

"European Application Serial No. 10723422.1, Office Action mailed Nov. 14, 2011", 2 pgs.

"European Application Serial No. 10723422.1, Response filed May 24, 2012 to Office Action mailed Nov. 14, 2011", 6 pgs.

* cited by examiner

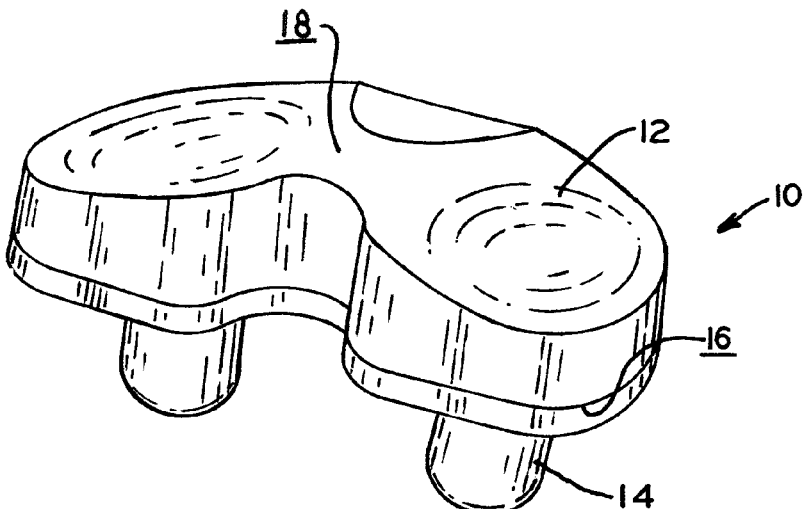
FIG_1
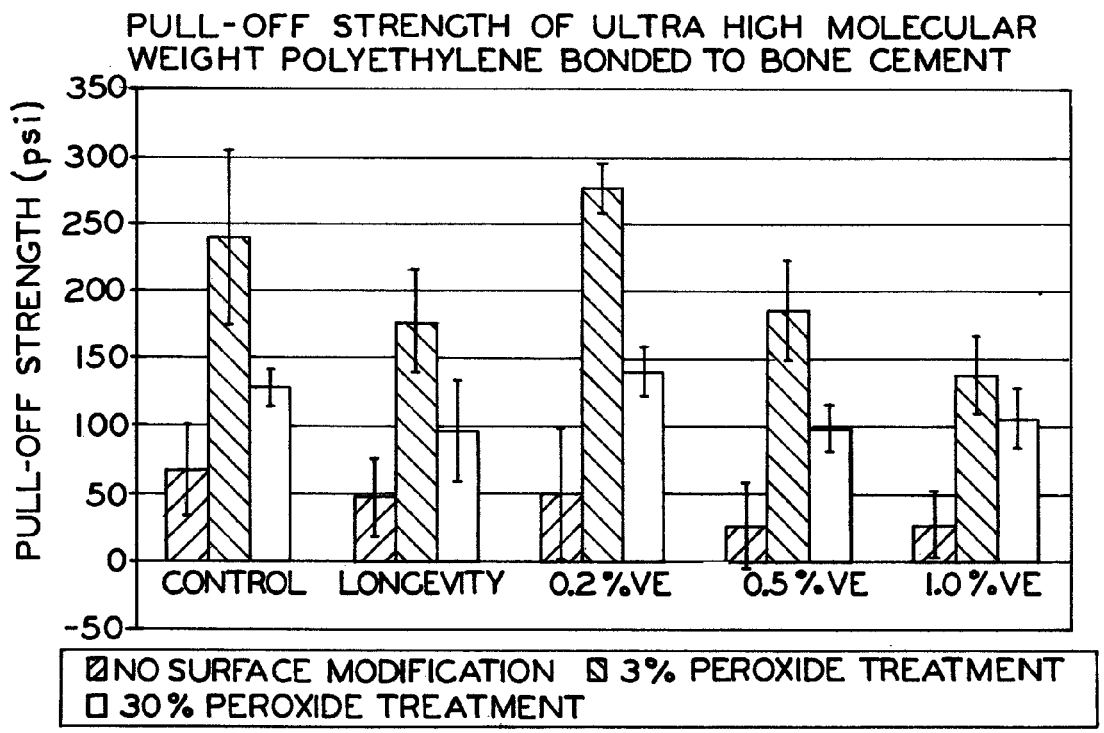
FIG_2

SURFACE MODIFICATION OF ULTRAHIGH MOLECULAR WEIGHT POLYETHYLENE

BACKGROUND

1. Field of the Invention

The present invention relates to polymers and, particularly, to the surface modification of polymers.

2. Description of the Related Art

Ultrahigh molecular weight polyethylene (UHMWPE) is commonly used to form orthopedic implant components, such as tibial, patella, acetabular, and glenoid components. In order to secure a UHMWPE component to a bone in a patient's body, polymethylmethacrylate (PMMA) bone cement may be used. PMMA bone cement secures a UHMWPE component to a patient's bone by mechanical fixation. Specifically, the PMMA is received within surface irregularities in the bone and in the UHMWPE component. As the PMMA polymerizes, it creates a mechanical interlock between the bone and the UHMWPE component. As a result, fixation of the UHMWPE component to the bone is primarily reliant on the surface geometry of the UHMWPE component and the bone. In order to improve the mechanical interlock between the UHMWPE component and the bone, recessed or protruding areas may be manufactured into the UHMWPE component to provide for the receipt of additional PMMA bone cement.

SUMMARY

The present invention relates to polymers and, specifically, to surface modification of polymers. In one exemplary embodiment, the present invention increases the bond strength of polymeric components, such as UHMWPE components, to polymeric or acrylic bone cement, such as PMMA bone cement, by creating a chemical bond between the UHMWPE components and the PMMA bone cement. Specifically, in one exemplary embodiment, a surface of the UHMWPE component that is to be bonded to PMMA bone cement is treated with an oxidizing agent, such as an aqueous solution of hydrogen peroxide. In one exemplary embodiment, the UHMWPE component is treated with hydrogen peroxide by swabbing the surface of the UHMWPE component with the hydrogen peroxide solution. The surface of the UHMWPE component may then be dried and PMMA bone cement applied to the surface of the UHMWPE component. Additionally, if two different UHMWPE components are to be bonded together with PMMA bone cement, the surfaces of both of the UHMWPE components that are to be bonded together may be treated with hydrogen peroxide.

In one exemplary embodiment, the techniques of the present invention may be utilized in conjunction with an antioxidant stabilized polymer, such as an antioxidant stabilized UHMWPE. For example, an antioxidant stabilized UHMWPE may be formed by mechanically blending or otherwise combining UHMWPE with an antioxidant, such as tocopherol, prior to forming the UHMWPE component. In this embodiment, the antioxidant stabilized UHMWPE component may be treated with hydrogen peroxide prior to using PMMA bone cement to secure the antioxidant stabilized UHMWPE component to a bone or to another UHMWPE component, whether antioxidant stabilized or not. As a result of the hydrogen peroxide surface treatment, the bond strength between the antioxidant stabilized UHMWPE component and the PMMA bone cement is increased.

Advantageously, by treating a surface of a UHMWPE component or an antioxidant stabilized UHMWPE component with an oxidizing agent, such as hydrogen peroxide, and then utilizing polymeric or acrylic bone cement, such as PMMA bone cement, to secure the treated surface of the UHMWPE to a bone or other object, the bonding strength between the PMMA and the UHMWPE component is substantially increased. This may allow for an increase in the number of orthopedic components that may be made at least partially or entirely of UHMWPE or antioxidant stabilized UHMWPE.

In one form thereof, a method is provided for treating a polymer surface to increase adhesion of bone cement. The method includes the steps of providing an aqueous solution comprising an oxidizing agent; coating a surface of a polymer with the solution to form a treated surface; positioning the polymer adjacent to one of an orthopedic component and a bone; and placing bone cement between the treated surface of the polymer and the one of the orthopedic component and the bone to bond the polymer to the one of the orthopedic component and the bone.

In another form thereof, a method is provided for treating an orthopedic implant to increase adhesion of bone cement. The method includes the steps of providing an orthopedic implant comprising a polymer, the implant having a mating surface; providing an aqueous hydrogen peroxide solution; applying the hydrogen peroxide solution to the mating surface of the orthopedic implant to form a treated surface; and securing the orthopedic implant to an adjacent component by placing bone cement between the treated surface of the orthopedic implant and the adjacent component.

In yet another form thereof, an orthopedic assembly is provided including: an orthopedic implant including a polymer, the orthopedic implant having a treated surface formed by coating a surface of the orthopedic implant with a hydrogen peroxide solution; and a layer of bone cement that contacts the treated surface of the orthopedic implant.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 1 is a perspective view of an exemplary orthopedic prosthesis of the present invention;

FIG. 2 is a bar chart showing the pull-off strength of 1.3 inch diameter UHMWPE and antioxidant stabilized UHMWPE cylinders bonded to bone cement with no surface modification and with different hydrogen peroxide surface treatments.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION

Figure 3:
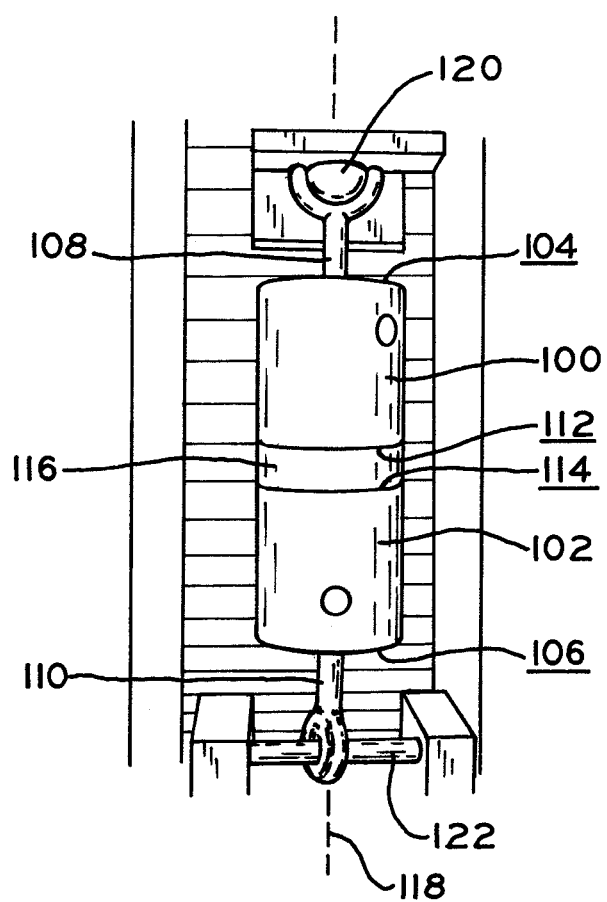
FIG. 3 is a perspective view of a pull-off testing apparatus showing opposing 1.3 inch diameter UHMWPE cylinders secured to one another by PMMA bone cement.

Polymers, such as UHMWPE are commonly used to form medical devices, such as orthopedic prostheses. For example, UHMWPE may be used to form the entirety of a medical device, such as a patella implant. Or, as shown in FIG. 1, UHMWPE may be used to form a component of a medical device, such as articular surface component 12 of tibial implant 10, while tray component 14 of tibial implant 10 may be formed of a different material, such as metal. Additionally, antioxidant stabilized UHMWPE may also be used to form medical devices.

In order to form an antioxidant stabilized UHMWPE, UHMWPE powder may be combined with an antioxidant. By forming a medical device from an antioxidant stabilized polymer, some of the free radicals in the polymer are quenched, which reduces oxidation and, correspondingly, increases the useful life of the polymer. For example, UHMWPE may be formed to include an antioxidant such as vitamin C, lycopene, honey, 6-hydroxy-2,5,7,8-tetramethylchroman-2-carboxylic acid, disulfides (e.g. nonylphenol disulfide), phosphites, hindered amines, phenols, cyclodextrins, flavonoids, and/or tocopherol, i.e., Vitamin E. Additionally, any tocopherol may be used, such as d-α-tocopherol, d/l-α-tocopherol, or α-tocopherol acetate. Thus, unless other specifically specified herein, the term "tocopherol" in its generic form refers to all tocopherols. Exemplary methods for combining UHMWPE with antioxidants are disclosed in co-pending U.S. Patent Publication No. 2008/0319137, entitled "ANTIOXIDANT STABILIZED CROSSLINKED ULTRA-HIGH MOLECULAR WEIGHT POLYETHYLENE FOR MEDICAL DEVICE APPLICATIONS", filed Apr. 10, 2008, assigned to the assignee of the present invention, the entire disclosure of which is expressly incorporated by reference herein.

In combining UHMWPE and tocopherol to form an antioxidant stabilized UHMWPE, any mechanism and/or process capable of achieving a substantially homogenous blend of the components may be utilized. In one exemplary embodiment, solvent blending is utilized. In solvent blending, tocopherol is mixed with a volatile solvent to lower the viscosity of the tocopherol and facilitate homogenous blending of the tocopherol with the UHMWPE. Once the tocopherol is mixed with the solvent, the tocopherol/solvent mixture may be combined with the UHMWPE, such as with a cone mixer. The solvent is then evaporated, leaving only the antioxidant stabilized UHMWPE. In another exemplary embodiment, tocopherol may be blended with UHMWPE by precision coating or atomization. For example, tocopherol may be precision coated onto the UHMWPE powder using a MP-1 MULTI-PROCESSOR™ Fluid Bed connected to a laboratory module Precision Coater available from Niro Inc. of Columbia, Md. MULTI-PROCESSOR™ is a trademark of Niro Inc.

In another exemplary embodiment, low intensity mixing may be used. Low intensity, i.e. low shear, mixing may be performed using a Diosna P100 Granulator, available from Diosna GmbH of Osnabrück, Germany, a subsidiary of Multimixing S.A. In another exemplary embodiment, high shear mixing may be used. High shear mixing of UHMWPE and tocopherol may be achieved using a RV02E or a R05T High Intensity Mixer, both commercially available from Eirich Machines of Gurnee, Ill. Alternatively, high shear mixing may be achieved using a Collette ULTIMAPRO™ 75 One Pot Processor available from Niro, Inc. of Columbia, Md. ULTIMAPRO™ is a trademark of Niro, Inc. Based on the results of testing the above identified methods useful for combining UHMWPE and tocopherol, high shear mixing appears to provide favorable results, including an acceptable homogeneity and a low number of indications, i.e., areas of high tocopherol concentrations relative to the surrounding areas as determined by visual inspection under ultraviolet light or by chemical measurements, such as infrared spectroscopy or gas chromatography. Additionally, in other exemplary embodiments, fluidized bed, emulsion polymerization, electrostatic precipitation, wetting or coating of particles, and/or master batch blending may be used to combine the UHMWPE and tocopherol.

Irrespective of the method used to combine the UHMWPE and tocopherol to form the antioxidant stabilized UHMWPE, the components are combined in ratios necessary to achieve a tocopherol concentration of between 0.01 weight percent (wt. %) and 3 wt. %. In exemplary embodiments, the tocopherol concentration may be as low as 0.01 wt. %, 0.05 wt. %, 0.1 wt. %, 0.25 wt. %, and 0.5 wt. % or as high as 0.6 wt. %, 0.8 wt. %, 1.0 wt. %, 2.0 wt. %, and 3.0 wt. %, for example. In determining the appropriate amount of tocopherol for inclusion in an antioxidant stabilized UHMWPE, two competing concerns exist. Specifically, the amount selected must be high enough to quench free radicals in the UHMWPE, but must also be low enough to allow sufficient crosslinking so as to maintain acceptable wear properties of the antioxidant stabilized UHMWPE. In one exemplary embodiment, a range of tocopherol from 0.1 to 0.6 wt. % is used to successfully quench free radicals while still maintaining acceptable wear properties.

As indicated above, polymeric or acrylic bone cement, such as PMMA bone cement, is commonly used to secure a UHMWPE component to bone or to another orthopedic component, which may be formed of UHMWPE, metal, ceramic, or other biocompatible materials. For example, during a revision surgery, a surgeon may ream out a portion of an old, antioxidant stabilized UHMWPE component and utilize PMMA bone cement to bond a new UHMWPE component to the remaining portion of the old, antioxidant stabilized UHMWPE component. As another example, and as shown in FIG. 1, a surgeon may utilize PMMA bone cement to bond articular surface component 12 onto tray component 14 of tibial implant 10. However, due to the free radical scavenging properties of antioxidants, such as tocopherol, free radical polymerization of the PMMA bone cement may be inhibited by the antioxidant near the surface of the antioxidant stabilized UHMWPE component. PMMA bone cement may include methylmethacrylate (MMA), polymethylmethacrylate (PMMA), esters of methacrylic acid, or copolymers containing polymethylmethacrylate (PMMA) and polystyrene.

In order to counteract the free radical scavenging effect of the antioxidant and the antioxidant stabilized UHMWPE component, an oxidizing agent such as hydrogen peroxide may be applied to the surface of the antioxidant stabilized UHMWPE component that will receive PMMA bone cement. The surgeon may avoid applying hydrogen peroxide to other surfaces of the antioxidant stabilized UHMWPE component, including the articulating surface. In the illustrated embodiment of FIG. 1, for example, the surgeon may apply hydrogen peroxide to the underside 16 of articular surface component 12 that will receive PMMA bone cement for bonding surface component 12 onto tray component 14 of tibial implant 10. The surgeon may avoid applying hydrogen peroxide to articulating surface 18 of articular surface component 12. By treating the surface of the UHMWPE component with an oxidizing agent such as hydrogen peroxide, the bond strength of the PMMA bone cement to the antioxidant stabilized UHMWPE component is increased. A detailed analysis of the improvement in the bonding strength of the PMMA bone cement to the antioxidant stabilized UHMWPE is set forth in the examples below.

In addition to hydrogen peroxide, other oxidizing agents that may be used to treat UHMWPE or antioxidant stabilized UHMWPE in the manner described in detail herein include: oxygen, ozone, peroxidases, carbamide peroxide, sodium percarbonate, calcium peroxide, magnesium peroxide, potassium monopersulfate, sodium perborate monohydrate, ozonide, sulfuric acid, nitric acid, citric acid, fluorosulfonic acid, sulfur trioxide, potassium permanganate, and/or cupric salts. Compared to other oxidizing agents, hydrogen peroxide may be more readily available, less expensive, less corrosive, and safer to use in an operating room.

Along with the oxidizing agent, the UHMWPE component may also be treated with a catalyst that encourages decomposition of the oxidizing agent. For example, the UHMWPE component may be treated with hydrogen peroxide and catalase, which functions to catalyze the decomposition of hydrogen peroxide to water and oxygen.

Advantageously, by utilizing hydrogen peroxide to treat the surface of an antioxidant stabilized UHMWPE component, the bond strength of the PMMA bone cement to the UHMWPE component is increased. Additionally, since hydrogen peroxide is readily available and safe to use in an operating room, as discussed above, a surgeon may apply a hydrogen peroxide treatment to the antioxidant stabilized UHMWPE component during or just before surgery. Alternatively, in one exemplary embodiment, a hydrogen peroxide treatment is applied to the antioxidant stabilized UHMWPE component by the manufacturer prior to receipt of the antioxidant stabilized UHMWPE component by the surgeon.

While the inventors of the present invention originally believed that a hydrogen peroxide treatment may work to counteract the free radical scavenging effects of an antioxidant stabilized UHMWPE in inhibiting the polymerization of PMMA bone cement, the corollary is that no increase in the bonding strength to PMMA bone cement of a UHMWPE that is not antioxidant stabilized and that is treated with hydrogen peroxide would have been expected. However, as set forth in the examples below, hydrogen peroxide treatment of a UHMWPE component that is not antioxidant stabilized resulted in a clear increase in the bonding strength of PMMA to the UHMWPE component's surface. As a result, the inventors now believe that the oxidizing agent treatment permanently modifies the surface of the UHMWPE component to increase the bonding strength between the PMMA bone cement and the UHMWPE component. This belief is supported by the fact that the beneficial effects that result from hydrogen peroxide treatment are still present after the hydrogen peroxide surface treatment has been allowed to dry. Thus, the present inventors believe that the effects are not a result of hydrogen peroxide being present on the surface of the UHMWPE component at the time of bonding to the PMMA bone cement, but are the result of a permanent surface modification of the UHMWPE component.

While the exact mechanism that results in the increase in bonding strength of PMMA bone cement to UHMWPE that has been treated with hydrogen peroxide is unknown, the surface treatment is thought to cause oxidation of the surface of the UHMWPE that results in the formation of alcohols, ketones, and carboxylic acids. This makes the surface of the UHMWPE hydrophilic, which increases the wettability of the UHMWPE. Additionally, peroxides can form free radicals on the surface of the UHMWPE that react with the methyl methacrylate monomer of PMMA to create a grafted structure. Further, it is believed that the hydrogen peroxide surface treatment may also loosening some of the low molecular weight polyethylene chains, resulting in surface micro-roughening.

In order to apply a hydrogen peroxide treatment to the surface of a UHMWPE or antioxidant stabilized UHMWPE component, the surface of the UHMWPE component may be swabbed with an aqueous hydrogen peroxide solution or the surface of the UHMWPE component may be submersed into a bath of the hydrogen peroxide solution. In exemplary embodiments, the concentration of hydrogen peroxide may be as low as 0.5 wt. % and as high as 30 wt. %. For example, in exemplary embodiments, the concentration of hydrogen peroxide in the aqueous hydrogen peroxide solution may be as low as 0.5 wt. %, 1.0 wt. %, 1.5 wt. %, 2.0 wt. %, and 2.5 wt. %, or as high as 3.0 wt. %, 4.0 wt. %, 5.0 wt. %, 10 wt. %, 15 wt. %, 20 wt. %, and 30 wt. %.

While described in detail herein with specific reference to UHMWPE and, particularly, to antioxidant stabilized UHMWPE, hydrogen peroxide treatment may also be used with other polymers, whether or not the polymers are antioxidant stabilized, such as ethylene vinyl alcohol (EVA), polycarbonate, and polyaryletherketones (PAEK), such as polyetheretherketone (PEEK), to increase the bonding strength of the polymers with bone cement.

The following non-limiting examples illustrate various features and characteristics of the present invention, which is not to be construed as limited thereto.

EXAMPLE 1

Effect of Hydrogen Peroxide Treatment on the Pull-Off Strength of UHMWPE

The first example illustrates the effect of hydrogen peroxide treatment on the pull-off strength of UHMWPE.

The following abbreviations are used throughout this section unless otherwise indicated.

TABLE 1

Abbreviations

| Abbreviation | Full Word |
| --- | --- |
| UHMWPE | ultrahigh molecular weight polyethylene |
| PMMA | polymethylmethacrylate |
| wt. % | weight percent |
| psi | pounds per square inch |
| T-Test | two-sample assuming unequal variances |
| VE | tocopherol |
| stdev | standard deviation |

An investigation into the pull-off strength of UHMWPE bonded to PMMA bone cement with and without antioxidant stabilization and before and after surface modification with hydrogen peroxide was investigated.

In order to prepare antioxidant stabilized UHMWPE for the test, GUR 1050 medical grade UHMWPE powder was obtained from Ticona, having North American headquarters in Florence, Ky. d/l-α-tocopherol was obtained from DSM Nutritional Products, Ltd., of Geleen, Netherlands. The GUR 1050 was mechanically blended with the d/l-α-tocopherol and consolidated by Quadrant of Lenzburg, Switzerland. The GUR 1050 resin was mixed with d/l-α-tocopherol to create three distinct antioxidant stabilized UHMWPE blends, one having a 0.2 wt. % concentration of d/l-α-tocopherol, another with a 0.5 wt. % concentration of d/l-α-tocopherol, and a third with a 1.0 wt. % concentration of d/l-α-tocopherol. The resulting antioxidant stabilized UHMWPE blends were then heated to 40° C. and subjected to 150 kGy dose of electron beam irradiation at Studer AG of Däniken, Switzerland, to cause crosslinking of the antioxidant stabilized UHMWPE blends. In addition to the three distinct concentrations of crosslinked, antioxidant stabilized UHMWPE, a control sample, taken from a bar of conventional UHMWPE formed from GUR 1050 that was not crosslinked, and a sample of Longevity® Crosslinked UHMWPE, commercially available from Zimmer, Inc., of Warsaw, Ind., were also tested for comparison. Longevity® is a registered trademark of Zimmer, Inc.

Each of the five different types of UHMWPE samples were then compression molded into bars. The bars were then turned on a lath to form 1.3 inch diameter cylinders, which were then cut into a series of mating cylinder halves 100, 102, as shown in FIG. 3, each cylinder half 100, 102, having a length of approximately 1.3 inches. A pilot hole (not shown) was then drilled into one end 104, 106, of each cylinder half 100, 102. A threaded eye bolt 108, 110, was then threaded into the pilot hole in one end 104, 106, of each of the opposing halves 100, 102, of the UHMWPE cylinder pairs. The other end 112, 114, of each of the opposing halves 100, 102, of the UHMWPE cylinder pairs were then prepared for the receipt of PMMA bone cement 116. Specifically, the end surfaces 112, 114, of the opposing halves 100, 102, of the UHMWPE cylinder pairs opposite the eye bolts 108, 110, were faced off on a lathe to ensure that the surfaces to be cemented were substantially flat, lied in a direction substantially perpendicular to the cylinder axes 118, and had a uniform surface roughness.

To prevent excess heating of the UHMWPE cylinders, each cylinder was cooled by a cold air gun during the machining process. The cutting tool of the lathe was cleaned using isopropyl alcohol before each UHMWPE cylinder was machined.

Once machined, if a hydrogen peroxide treatment was to be applied to the UHMWPE cylinder pair 100, 102, the end surfaces 112, 114, of the opposing halves 100, 102, of the UHMWPE cylinder pair opposite the eye bolts 108, 110, were swabbed with a hydrogen peroxide solution of the desired concentration, i.e., either 3% hydrogen peroxide solution or 30% hydrogen peroxide solution, using a clean cotton swab until the surface 112, 114, was sufficiently wetted. The end surfaces 112, 114, were then dried by blotting the end surfaces 112, 114, with lint free wipes to remove any hydrogen peroxide solution present on the end surfaces 112, 114, of the UHMWPE cylinders 100, 102.

No cleaning of the machined surfaces 112, 114, of the UHMWPE cylinders 100, 102, was performed prior to cementing the pairs of cylinders 100, 102, together, as described in detail below, and care was taken to keep the surfaces 112, 114, free from contamination prior to cementing.

To prepare the opposing halves 100, 102, of the UHMWPE cylinder pairs for the receipt of bone cement 116, a length of masking tape was cut and positioned, with the adhesive side facing upward, on a piece of paper having a series of perpendicular lines drawn on the paper to facilitate alignment of the tape. The tape was then marked with a pen to delineate a centered, uniform 0.35 inch gap extending across the tape in a direction parallel to the longitudinal axis of the tape. Each of the opposing halves 100, 102, of a UHMWPE cylinder pair was aligned with its end surface 112, 114, opposite the eye bolt 108, 110, aligned to extend along one of the marks on the tape, such that the cylinder axis 118 of the opposing halves 100, 102, was perpendicular to the longitudinal axis of the tape, and with the openings of the eyebolts 108, 110, offset by ninety degrees of rotation relative to the other on the cylinders common axis 118. The cylinder halves 100, 102, were then rolled along the tape to wrap a portion of the tape around each of the opposing cylinder halves 100, 102, and to form a gap of 0.35 inches between the end surfaces 112, 114, of the opposing cylinder halves 100, 102. An inlet port was then formed in the tape by cutting 3 sides of a square having approximately 0.25 inch sides in the tape to form a flap.

PMMA bone cement 116 was then mixed in an open bowl, transferred to a bone cement cartridge, and injected through a small nozzle positioned through the flap in the masking tape to inject PMMA bone cement 116 into the gap between the opposing halves 100, 102, of the UHMWPE cylinder pairs. The flaps of each of the cylinder pairs 100, 102, were then closed and the PMMA bone cement 116 was allowed to cure for sixty minutes. The PMMA bone cement 116 was Osteobond® copolymer bone cement, catalog number 1101-08, lot number 60438914, commercially available from Zimmer, Inc., of Warsaw, Ind. Osteobond® is a registered trademark of Zimmer, Inc. After the passage of 60 minutes, the masking tape was removed from the UHMWPE cylinders 100, 102.

Then, referring to FIG. 3, the eye bolts 108, 110, extending from the ends of the opposing halves 100, 102, of the UHMWPE cylinders were secured to an Instron Mechanical Tester, model number 3345, to determine the failure point of the bond between the PMMA bone cement 116 and the opposing halves 100, 102, of the UHMWPE cylinder. Specifically, one of the opposing halves 102 of the UHMWPE cylinder pairs were fixed to the Instron Mechanical Tester by passing a bolt 122 through the eye bolt 110 secured to the cylinder 102 and through a bottom clevis mounted to a bottom plate of the Instron Mechanical Tester. The other one of the opposing halves 100 of the UHMWPE cylinder pairs was fixed to the Instron Mechanical Tester by passing a bolt 120 through the eye bolt 108 secured to the cylinder 100 and through a top clevis that was attached to a swivel coupling connected to a load cell on a crosshead of the Instron Mechanical Tester. A ninety degree offset was employed between the eyebolt 108 of the UHMWPE cylinder and the axis of rotation of the swivel coupling to ensure that the force applied to the UHMWPE cylinders 100, 102, was uniform across the UHMWPE-bone cement interfaces 112, 114. A tensile testing method with a crosshead rate of 0.050 inches per minute was used and data regarding the peak force applied to the cylinders during movement of the crosshead until fracture was recorded to determine the pull-off strength in pounds at the UHMWPE-bone cement interfaces 112, 114. All of the specimens tested failed at one of the two UHMWPE-bone cement interfaces 112, 114.

As shown in the results, set forth in FIG. 2 and Tables 2-4, below, by treating the surfaces of the opposing halves 100, 102, of the UHMWPE cylinders with hydrogen peroxide prior to securing the same together with PMMA bone cement 116, the pull-off strength, i.e., the amount of force necessary to cause a failure of the UHMWPE/PMMA bone cement bond, was substantially increased. As indicated in Tables 2-4 below, the test of the bond strength was repeated until the test had been performed with no hydrogen peroxide treatment, a hydrogen peroxide treatment with a 3 wt. % hydrogen peroxide solution, and a hydrogen peroxide treatment with a 30 wt. % hydrogen peroxide treatment, as indicated above.

TABLE 2

Pull-Off Strength (psi) without Surface Treatment

| | Test No. | Control | Longevity | Antioxidant Stabilized UHMWPE (0.2 wt. % VE) | Antioxidant Stabilized UHMWPE (0.5 wt. % VE) | Antioxidant Stabilized UHMWPE (1.0 wt. % VE) |
|---|---|---|---|---|---|---|
| | 1 | 64.04 | 58.18 | 0.31 | 32.55 | 12.22 |
| | 2 | 41.32 | 56.42 | 8.45 | 17.49 | 15.58 |
| | 3 | 135.26 | 16.01 | 109.75 | 1.31 | 38.26 |
| | 4 | 32.53 | 12.14 | 7.61 | 10.92 | 8.59 |
| | 5 | 106.50 | 54.38 | 25.12 | 113.43 | 85.90 |
| | 6 | 60.86 | 41.03 | 12.23 | 28.43 | 0.08 |
| | 7 | 25.02 | 20.09 | 55.96 | 0.52 | 16.78 |
| | 8 | 87.20 | 104.04 | 99.51 | 26.57 | 29.79 |
| | 9 | 57.16 | 76.21 | 48.43 | 31.42 | 23.58 |
| | 10 | 62.77 | 39.94 | 133.66 | 7.66 | 46.31 |
| | Average | 67.27 | 47.84 | 50.10 | 27.03 | 27.71 |
| | stdev | 33.99 | 28.58 | 48.42 | 32.67 | 24.72 |
| T-Test | Control P | | 0.185 | 0.373 | 0.015 | 0.009 |
| | Longevity P | 0.185 | | 0.901 | 0.147 | 0.109 |

TABLE 3

Pull-Off Strength (psi) with 3 wt. % Hydrogen Peroxide Surface Treatment

| | Test No. | Control | Longevity | Antioxidant Stabilized UHMWPE (0.2 wt. % VE) | Antioxidant Stabilized UHMWPE (0.5 wt. % VE) | Antioxidant Stabilized UHMWPE (1.0 wt. % VE) |
|---|---|---|---|---|---|---|
| | 1 | | 219.27 | 257.10 | 195.97 | 115.67 |
| | 2 | 164.71 | 187.03 | 279.29 | 172.95 | 116.48 |
| | 3 | 284.50 | 174.51 | 265.05 | 231.35 | 177.19 |
| | 4 | 267.08 | 127.28 | 298.94 | 144.06 | 144.04 |
| | Average | 238.76 | 177.02 | 275.10 | 186.08 | 138.35 |
| | stdev | 64.72 | 38.15 | 18.36 | 36.90 | 29.06 |
| T-Test | 3 wt. % P | 0.048 | 0.004 | 0.000 | 0.001 | 0.001 |
| | Increase | 355% | 370% | 549% | 688% | 499% |

TABLE 4

Pull-Off Strength (psi) with 30 wt. % Hydrogen Peroxide Surface Treatment

| | Test No. | Control | Longevity | Antioxidant Stabilized UHMWPE (0.2 wt. % VE) | Antioxidant Stabilized UHMWPE (0.5 wt. % VE) | Antioxidant Stabilized UHMWPE (1.0 wt. % VE) |
|---|---|---|---|---|---|---|
| | 1 | 127.86 | 62.46 | 135.20 | 111.00 | 87.99 |
| | 2 | 114.34 | 91.04 | 159.56 | 106.77 | 100.19 |
| | 3 | 141.15 | 136.81 | 124.55 | 77.89 | 130.11 |
| | Average | 127.78 | 96.77 | 139.77 | 98.55 | 106.10 |
| | stdev | 13.41 | 37.50 | 17.95 | 18.02 | 21.67 |
| T-Test | 30 wt. % P | 0.001 | 0.128 | 0.001 | 0.003 | 0.006 |
| | Increase | 190% | 202% | 279% | 365% | 383% |

EXAMPLE 2

Effect of Hydrogen Peroxide Treatment on Wettability of UHMWPE

The second example illustrates the effect of hydrogen peroxide treatment on the wettability of UHMWPE.

UHMWPE samples were prepared from blocks of Durasul® crosslinked UHMWPE, commercially available from Zimmer, Inc., of Warsaw, Ind. Durasul® is a registered trademark of Zimmer, Inc. Some of the UHMWPE samples were swabbed with a 3% hydrogen peroxide solution, while others were left untreated.

The wettability of the UHMWPE samples was measured using two different test solutions—water and bovine serum. With water as the test solution, the average contact angle of the water droplets decreased from 88.89° on the untreated UHMWPE samples to 78.98° on the hydrogen peroxide treated UHMWPE samples, indicating increased wettability of the hydrogen peroxide treated UHMWPE samples. Similarly, with bovine serum as the test solution, the average contact angle of the bovine serum droplets decreased from 79.96° on the untreated UHMWPE samples to 78.59° on the hydrogen peroxide treated UHMWPE samples, indicating increased wettability of the hydrogen peroxide treated UHMWPE samples.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopedic assembly comprising:
    an orthopedic implant comprising antioxidant-stabilized ultra-high molecular weight polyethylene, the orthopedic implant having an oxidizing agent-modified surface formed by coating a surface of the orthopedic implant with a liquid comprising from about 0.5 wt % to about 10 wt % hydrogen peroxide; and
    a layer of bone cement that contacts the oxidizing agent-modified surface of the orthopedic implant.

2. The implant assembly of claim 1, wherein the polymer comprises at least one of ultrahigh molecular weight polyethylene, ethylene vinyl alcohol, polycarbonate, and polyetheretherketone.

3. The implant assembly of claim 1, wherein the bone cement comprises polymethylmethacrylate.

4. The implant assembly of claim 1, wherein the antioxidant comprises at least one of vitamin C, lycopene, honey, 6-hydroxy-2,5,7,8-tetramethylchroman-2-carboxylic acid, a disulfide, a phosphite, a hindered amine, a phenol, a cyclodextrin, a flavonoid, and a tocopherol.

5. The implant assembly of claim 1, wherein the antioxidant of the antioxidant stabilized polymer is present in an amount between 0.01 weight percent and 3 weight percent.

6. The implant assembly of claim 1, wherein the antioxidant of the antioxidant stabilized polymer is present in an amount between 0.1 weight percent and 0.6 weight percent.

7. The implant assembly of claim 1, wherein the liquid comprises a solution of hydrogen peroxide having a concentration of about 3 weight percent hydrogen peroxide.

8. The implant assembly of claim 1, wherein the orthopedic implant includes an articulating surface.

9. The implant assembly of claim 1, wherein a pull off strength between the treated surface and the layer of bone cement is at least 96 PSI.

10. An orthopedic assembly comprising:
    an orthopedic implant comprising antioxidant-stabilized ultrahigh molecular weight polyethylene, the orthopedic implant having an oxidizing agent-modified surface formed by coating a surface of the orthopedic implant with a hydrogen peroxide solution comprising from about 0.5 wt % to about 10 wt % hydrogen peroxide; and
    a layer of bone cement that contacts the oxidizing agent-modified surface of the orthopedic implant wherein the bone cement comprises polymethylmethacrylate.

11. The implant assembly of claim 10, wherein the antioxidant comprises at least one of vitamin C, lycopene, honey, 6-hydroxy-2,5,7,8-tetramethylchroman-2-carboxylic acid, a disulfide, a phosphite, a hindered amine, a phenol, a cyclodextrin, a flavonoid, and a tocopherol.

12. The implant assembly of claim 10, wherein the antioxidant of the antioxidant stabilized ultrahigh molecular weight polyethylene is present in an amount between 0.01 weight percent and 3 weight percent.

13. The implant assembly of claim 10, wherein the antioxidant of the antioxidant stabilized ultrahigh molecular weight polyethylene is present in an amount between 0.1 weight percent and 0.6 weight percent.

14. The implant assembly of claim 10, wherein the hydrogen peroxide solution has a concentration of about 3 weight percent hydrogen peroxide.

15. The implant assembly of claim 10, wherein the orthopedic implant includes an articulating surface.

16. The implant assembly of claim 10, wherein a pull off strength between the treated surface and the layer of bone cement is at least 96 PSI.

* * * * *